(12) United States Patent
Tulkis

(10) Patent No.: US 7,837,686 B1
(45) Date of Patent: Nov. 23, 2010

(54) SURGICAL CUTTING TOOL

(75) Inventor: Peter Tulkis, Paramus, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 855 days.

(21) Appl. No.: 11/614,615

(22) Filed: Dec. 21, 2006

(51) Int. Cl.
*A61B 17/32* (2006.01)

(52) U.S. Cl. ...................................... 606/81
(58) Field of Classification Search ............... 606/80, 606/81, 167, 180, 183
See application file for complete search history.

(56) References Cited

U.S. PATENT DOCUMENTS

| | | | | |
|---|---|---|---|---|
| 3,633,583 | A * | 1/1972 | Fishbein | 606/81 |
| 4,131,116 | A * | 12/1978 | Hedrick | 606/81 |
| 4,621,637 | A * | 11/1986 | Fishbein | 606/81 |
| 5,755,719 | A * | 5/1998 | Frieze et al. | 606/81 |
| 5,897,558 | A * | 4/1999 | Frieze et al. | 606/81 |
| 6,168,599 | B1 * | 1/2001 | Frieze et al. | 606/80 |
| 6,702,819 | B2 | 3/2004 | Lechot | |
| 6,979,335 | B2 * | 12/2005 | Lechot | 606/80 |
| 7,011,662 | B2 * | 3/2006 | Lechot et al. | 606/80 |
| 2003/0078587 | A1 | 4/2003 | Lechot et al. | |
| 2004/0049199 | A1 * | 3/2004 | Lechot et al. | 606/80 |
| 2004/0167528 | A1 * | 8/2004 | Schantz | 606/81 |
| 2006/0004371 | A1 | 1/2006 | Williams, III et al. | |

* cited by examiner

*Primary Examiner*—Thomas C Barrett
*Assistant Examiner*—Christopher Beccia
(74) *Attorney, Agent, or Firm*—Arthur Jacob

(57) ABSTRACT

A surgical cutting tool for cutting a seating surface of curved contour configuration in natural bone for receiving a component of a prosthetic implant at an implant site. The tool has cutting blades in a cutting blade construct placed within an arbor such that the cutting blades are supported by the arbor circumferentially spaced from one another, with cutting edges of the cutting blades exposed for cutting the seating surface. Stabilizers along the arbor stabilize the tool during a cutting operation, while channels in the arbor along the cutting blades carry away cut bone. The cutting blades are essentially flat, are economically manufactured from flat stock, are provided with a predetermined thickness and a cutting blade radius, and include cutting edges placed within the cutting blade construct circumferentially forward of the cutting blade radius to establish a gap between the cutting blade radius and a corresponding radius of the seating surface for providing an effective cutting profile along each cutting edge.

34 Claims, 15 Drawing Sheets

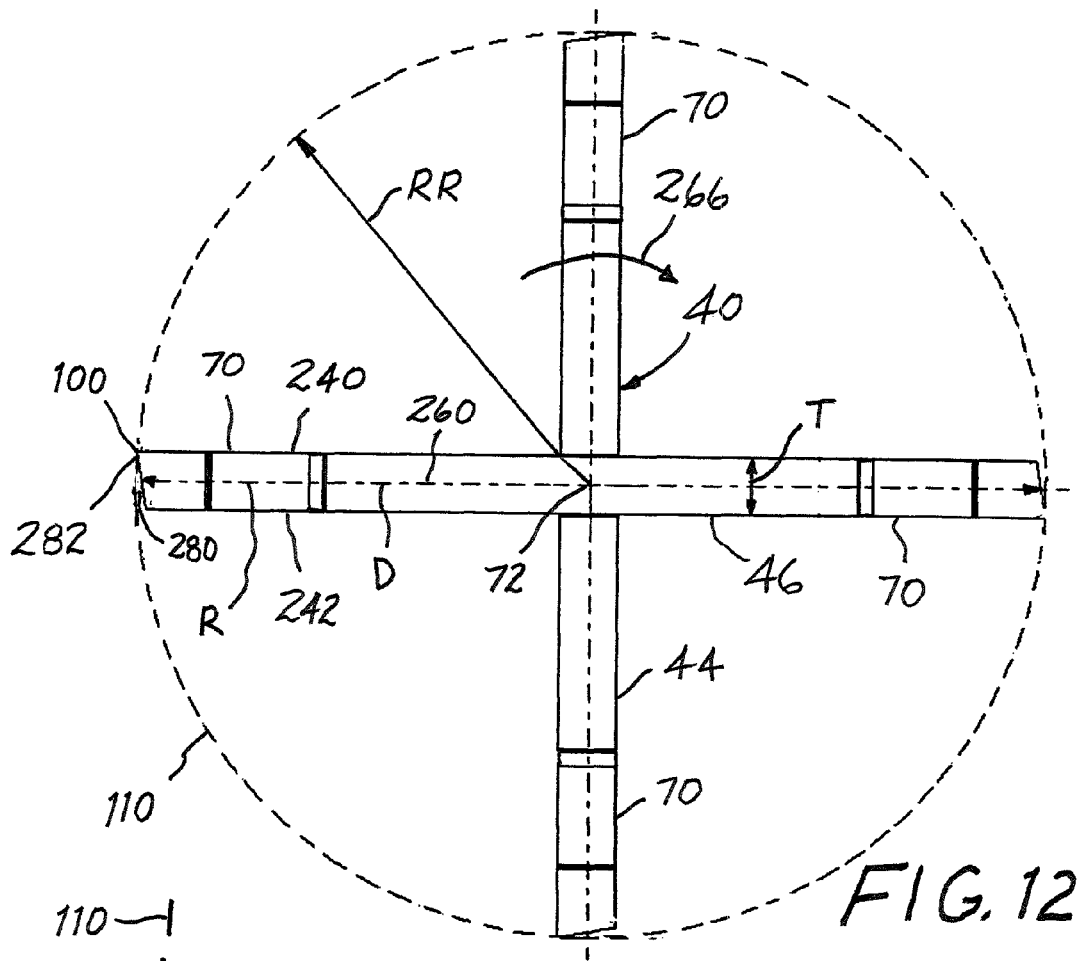
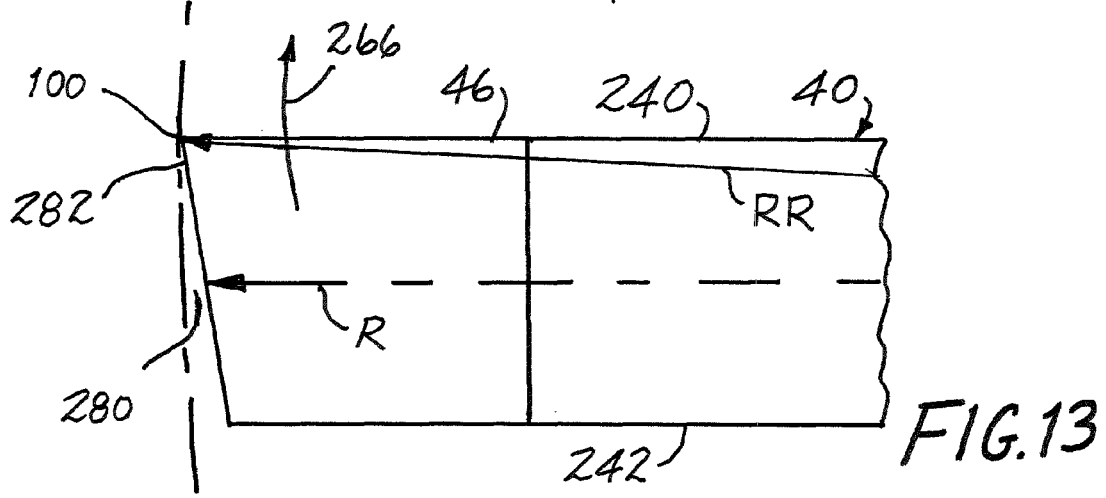

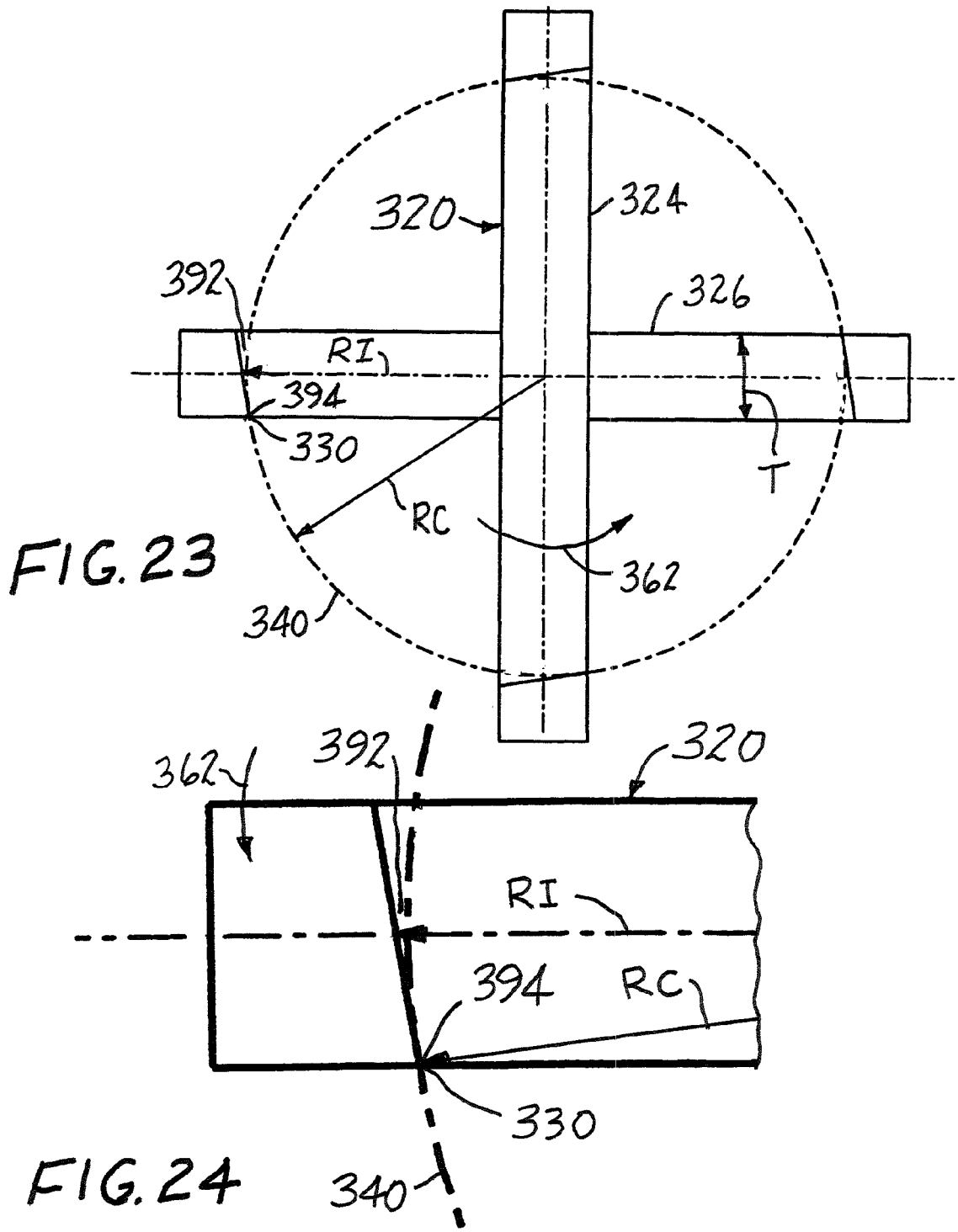

SURGICAL CUTTING TOOL

The present invention relates generally to the preparation of natural bone for the reception of a component of a prosthetic joint and pertains, more specifically, to a surgical cutting tool for establishing a seating surface having an appropriate contour configuration and surface characteristics for the reception and affixation of such an implant component in the natural bone.

A variety of surgical cutting tools currently are available for preparing a seating surface in the natural bone at an implant site for the reception of a component of a prosthetic joint to be implanted at the site. For example, in a commonly used current procedure for the preparation of the natural bone at an implant site of a prosthetic hip joint, the acetabulum is prepared with a reamer provided with a cutting surface having a generally hemispherical surface contour configuration corresponding to the contour configuration of the acetabular component to cut a seating surface in the acetabulum for the reception of the acetabular component. The cutting surface of such conventional reamers is constructed in the form of a hemispherical metal shell, usually drawn from a sheet of metal, and provided with a number of small cutting teeth punched from the shell in an outward direction to establish a corresponding number of cutting edges scattered throughout the cutting surface. The cutting teeth are placed in a staggered arrangement such that as the reamer is rotated, the cutting teeth follow overlapping circumferential paths in an effort to remove bone essentially throughout a concave hemispherical seating area suitable for the reception of the acetabular component.

These conventional acetabular reamers are prone to several drawbacks, some of which are outlined as follows: The manufacturing process which calls for forming a metal sheet into a domed hemispherical shell, and then punching the cutting teeth from the metal shell, requires manufacturing tolerances which do not provide a high degree of accuracy, so that the diameter of a reamer of any one particular size can vary considerably from a nominal dimension, allowing wider variations in the dimensions of the seating surface prepared at the implant site. Moreover, the nature of the manufacturing process itself renders the maintenance of even these manufacturing tolerances relatively costly. Further, as the cutting teeth wear and lose sharpness, surgeons tend to increase the force exerted on the reamer in order to achieve a desired cut; however, dulled teeth tend to remove bone in larger chunks of uncontrolled dimensions, as compared to smaller cuttings removed by sharper cutting edges, leading to an unwanted enlarged seat, as well as a seating surface interrupted by peaks and valleys left behind by the plurality of individual cutting teeth. These peaks and valleys decrease the contact area made available between an implanted acetabular component and the host bone at the implant site, to the detriment of the implant procedure, as well as the subsequent performance of the implant itself.

In addition, the construction in which sheet metal is drawn into a hemispherical shell requires the presence of an uninterrupted rim adjacent the equator of the hemispherical construction for purposes of maintaining structural integrity, so that no teeth are present around the circumference of the rim of the otherwise toothed shell. Consequently, the actual cutting surface area extends over less than a 180° hemisphere, resulting in the formation of an undersized ledge around the perimeter of the prepared seat, at the entrance to the seat. The undersized ledge will impede full seating of the acetabular component within the prepared bone, leaving a polar gap between the component and the seat, and can contribute to acetabular fractures during insertion of the acetabular component into the seat.

Still further, inaccuracies in the geometry of the prepared acetabulum can result in improper affixation of the acetabular component at the implant site, leading to inadvertent detachment and dislocation of an implanted acetabular component. Additionally, such inaccuracies can cause deleterious deformation of the acetabular component, affecting not only affixation, but subsequent performance of the prosthetic joint itself.

It has been suggested that these current conventional reamers can be replaced with surgical cutting tools having cutting elements in the form of plates with curved cutting edges which, upon rotation of the plates, will cut a seating surface of desired contour configuration. However, these proposed cutting tools heretofore have been costly to manufacture with the precision required for accomplishing an acceptable result, have been difficult to use, and therefore have not supplanted the widespread acceptance and use of the domed sheet metal construction described above.

The present invention overcomes the above-outlined drawbacks and attains several objects and advantages, some of which are summarized as follows: Enables a higher degree of accuracy, with increased ease, in the preparation of natural bone at an implant site for the reception of an implant component of a prosthetic joint; provides a less costly surgical cutting tool, readily manufactured to closer tolerances, for more effectively cutting an accurate seating surface, with increased ease, for an implant component of a prosthetic joint, and especially for the preparation of an acetabulum to receive an acetabular component; enables the establishment of a seating surface for the reception of an implant component, and especially an acetabular surface for the reception of an acetabular component, the seating surface being relatively smooth and uninterrupted by unwanted peaks and valleys so as to be more conducive to proper placement and affixation of the implant component; provides a construction in a surgical cutting tool for use in the preparation of an implant site, the tool being manufactured with such economy as to render the tool readily expendable, thereby enabling economical use of a new, freshly sharp cutting tool with each implant procedure.

The above objects and advantages, as well as further objects and advantages, are attained by the present invention which may be described briefly as a surgical cutting tool for cutting a seating surface in natural bone, the seating surface having a contour configuration for receiving a component of a prosthetic implant having a complementary contour configuration, the cutting tool comprising: a cutting blade construct including a central axis of rotation and at least one cutting element having at least one cutting edge spaced from the central axis in a radial direction, the cutting edge having a profile configuration dimensioned and configured such that upon rotation of the cutting blade construct about the central axis of rotation, the cutting edge will follow a cutting envelope having a contour configuration for corresponding to the contour configuration of the seating surface; and an arbor coupled with the cutting blade construct for rotation about the central axis of rotation with the cutting blade construct, the arbor having an external surface; the cutting blade construct being placed within the arbor with the cutting edge spaced radially away from the external surface of the arbor to expose the cutting edge for cutting the contour configuration of the seating surface, and the arbor extending circumferentially for supporting the cutting edge in circumferential directions; the external surface of the arbor including first surface portions extending along a support envelope spaced radially away from the cutting envelope such that upon rotation of the arbor during cutting of the seating surface the support envelope will be spaced radially from the natural bone, and second surface portions located circumferentially adjacent the cutting edge, and radially intermediate the support envelope and the cutting envelope to follow a stabilizing envelope for juxtaposition with the natural bone during cutting of the seating surface to stabilize the cutting blade construct while rotating the arbor and cutting blade construct about the central axis of rotation to cut the seating surface.

In addition, the present invention provides a surgical cutting tool for cutting a seating surface in natural bone, the seating surface having a contour configuration for receiving a component of a prosthetic implant having a complementary contour configuration, the cutting tool comprising: a cutting blade construct including a central axis of rotation and cutting elements having cutting edges spaced from one another in circumferential directions, and spaced from the central axis in radial directions, each cutting edge having a profile configuration dimensioned and configured such that upon rotation of the cutting blade construct about the central axis of rotation, the cutting edges will follow a cutting envelope having a contour configuration for corresponding to the contour configuration of the seating surface; and an arbor coupled with the cutting blade construct for rotation about the central axis of rotation with the cutting blade construct, the arbor having an external surface; the cutting blade construct being placed within the arbor with the cutting edges spaced radially away from the external surface of the arbor to expose the cutting edges for cutting the profile contour configuration of the seating surface, and the arbor extending circumferentially between the cutting elements for supporting the cutting edges spaced from one another in circumferential directions; each cutting element comprising a cutting blade of predetermined thickness, each cutting blade extending along a radius of the cutting envelope and having a leading face and a trailing face spaced circumferentially back from the leading face by the predetermined thickness of the cutting blade, the cutting blade extending from the central axis of rotation radially along a cutting blade radius, the relative dimensions of the cutting blade radius and a corresponding radius of the cutting envelope establishing a gap between the cutting blade radius and the cutting envelope and a cutting profile along the cutting blade, each gap being located circumferentially between a corresponding cutting edge and at least one of an adjacent leading face and an adjacent trailing face, such that upon rotation of the cutting blade construct to cut the seating surface, the cutting edge along the cutting profile will engage the natural bone along the cutting envelope circumferentially spaced from the one of the adjacent leading face and the adjacent trailing face.

Further, the present invention includes a surgical cutting tool for cutting a seating surface in natural bone, the seating surface having a contour configuration for receiving a component of a prosthetic implant having a complementary contour configuration, the cutting tool comprising: a cutting blade construct including a central axis of rotation and cutting elements having cutting edges spaced from one another in circumferential directions, and spaced from the central axis in radial directions, each cutting edge having a profile configuration dimensioned and configured such that upon rotation of the cutting blade construct about the central axis of rotation, the cutting edges will follow a cutting envelope having a contour configuration for corresponding to the contour configuration of the seating surface; and an arbor coupled with the cutting blade construct for rotation about the central axis of rotation with the cutting blade construct, the arbor having an external surface; the cutting blade construct being placed within the arbor with the cutting edges spaced radially away from the external surface of the arbor to expose the cutting edges for cutting the profile contour configuration of the seating surface, and the arbor extending circumferentially between the cutting elements for supporting the cutting edges spaced from one another in circumferential directions; each cutting element comprising a cutting blade extending along a radius of the cutting envelope, each cutting blade having a predetermined thickness, a leading face at the cutting edge for engaging the natural bone during cutting of the seating surface, and a trailing face spaced circumferentially back from the leading face by the predetermined thickness of the cutting blade, the cutting blade extending from the central axis of rotation radially along a cutting blade radius, the relative dimensions of the cutting blade radius and a corresponding radius of the cutting envelope establishing a gap between the cutting blade radius and the cutting envelope and a cutting profile along the cutting blade, each gap being located circumferentially behind a corresponding cutting edge, and the leading face being spaced circumferentially forward of the cutting blade radius such that upon rotation of the cutting blade construct to cut the seating surface, the cutting edge along the cutting profile will engage the natural bone along the cutting envelope circumferentially forward of the gap.

Still further, the present invention provides a surgical cutting tool for cutting a seating surface in natural bone, the seating surface having a contour configuration for receiving a component of a prosthetic implant having a complementary contour configuration, the cutting tool comprising: a cutting blade construct including a central axis of rotation and cutting elements having cutting edges spaced from one another in circumferential directions, and spaced from the central axis in radial directions, each cutting edge having a profile configuration dimensioned and configured such that upon rotation of the cutting blade construct about the central axis of rotation, the cutting edges will follow a cutting envelope having a contour configuration for corresponding to the contour configuration of the seating surface; and an arbor coupled with the cutting blade construct for rotation about the central axis of rotation with the cutting blade construct, the arbor having an external surface; the cutting blade construct being placed within the arbor with the cutting edges spaced radially away from the external surface of the arbor to expose the cutting edges for cutting the profile contour configuration of the seating surface, and the arbor extending circumferentially between the cutting elements for supporting the cutting edges spaced from one another in circumferential directions; the cutting blade construct being constructed of metal, and the arbor being constructed of a synthetic polymeric material.

The invention will be understood more fully, while still further objects and advantages will become apparent, in the following detailed description of preferred embodiments of the invention illustrated in the accompanying drawing, in which:

FIG. 12 is a diagrammatic view of a cutting blade construct of the tool;

FIG. 13 is an enlarged fragmentary view showing a portion of FIG. 12;

FIG. 23 is a diagrammatic view of the cutting blade construct of the tool; and

FIG. 24 is an enlarged fragmentary view showing a portion of FIG. 23.

Figure 1:
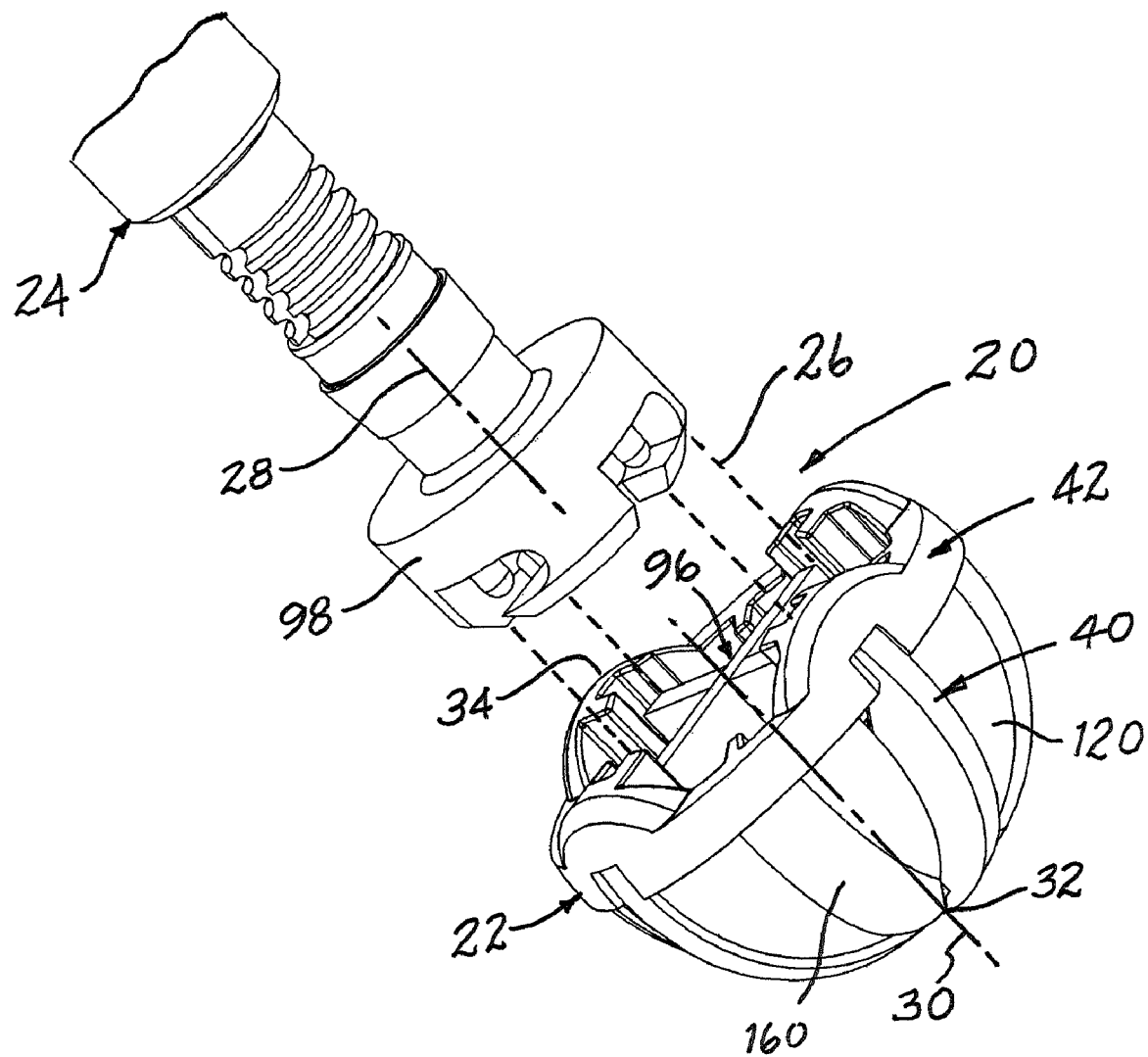
FIG. 1 is a pictorial view, partially exploded, showing a surgical cutting tool constructed in accordance with the present invention.

Referring now to the drawing, and especially to FIG. 1 thereof, a surgical cutting tool constructed in accordance with the present invention is shown at 20 and is seen to include a cutting head 22 and an operating handle 24. A coupling arrangement 26 selectively couples cutting head 22 to handle 24 such that upon rotation of the handle 24 about a longitudinal axis of rotation 28, cutting head 22 will be rotated about a central axis of rotation 30 which, in the illustrated embodiment, is coincident with axis of rotation 28.

Figure 2:
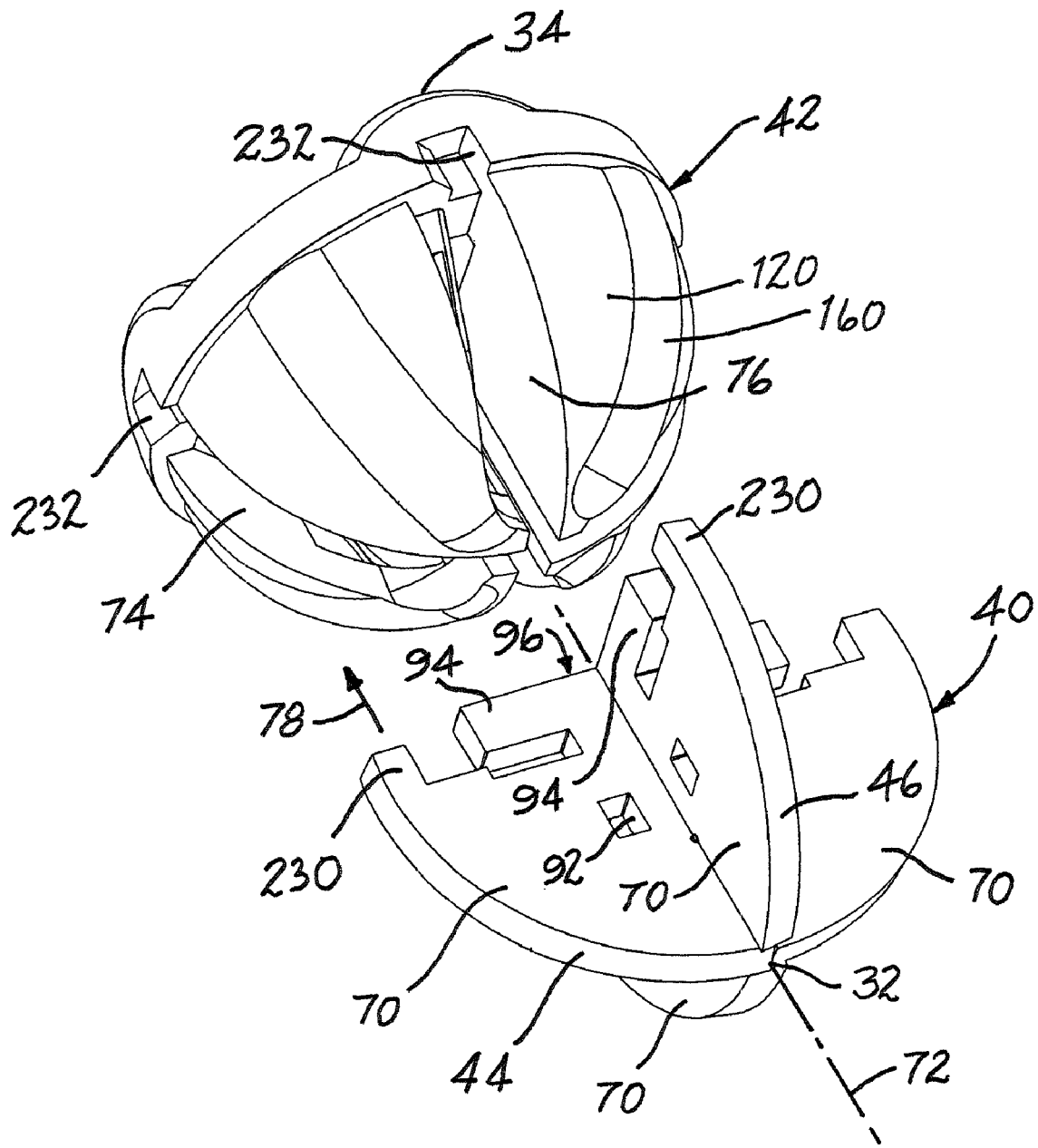
FIG. 2 is an exploded perspective view showing component parts of the surgical cutting tool.
Figure 3:
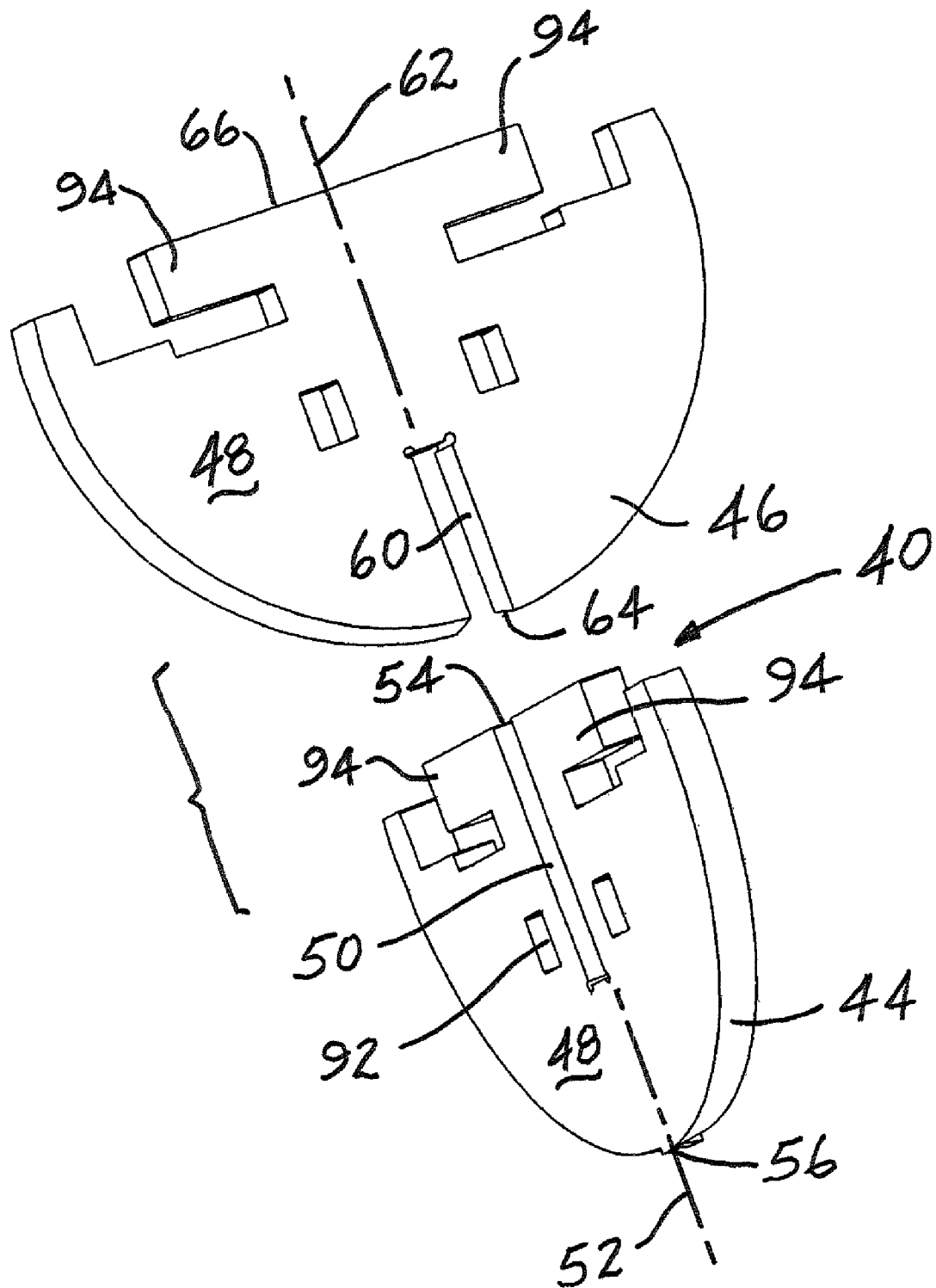
FIG. 3 is a further exploded perspective view showing component parts of the tool.
Figure 4:
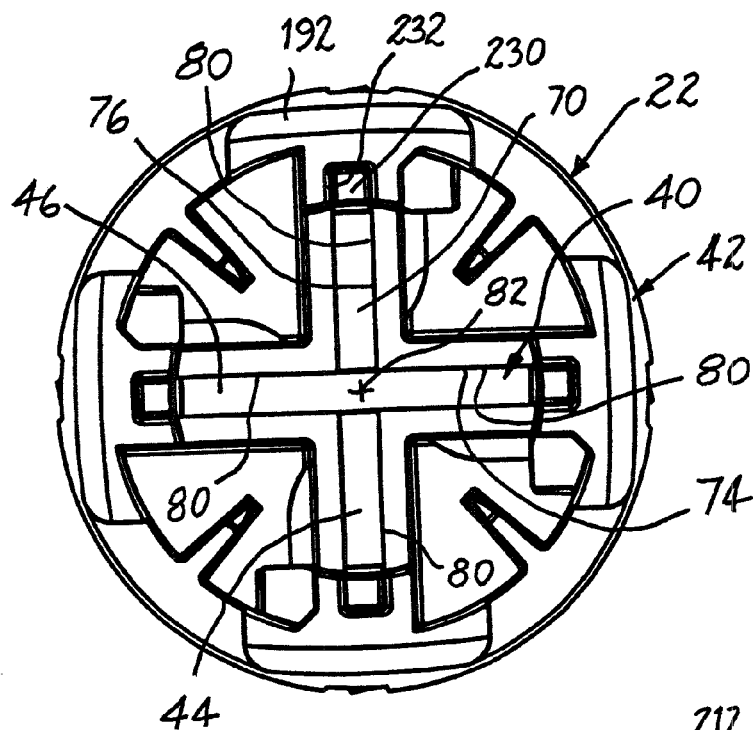
FIG. 4 is a top plan view of the cutting head of the surgical cutting tool.
Figure 5:
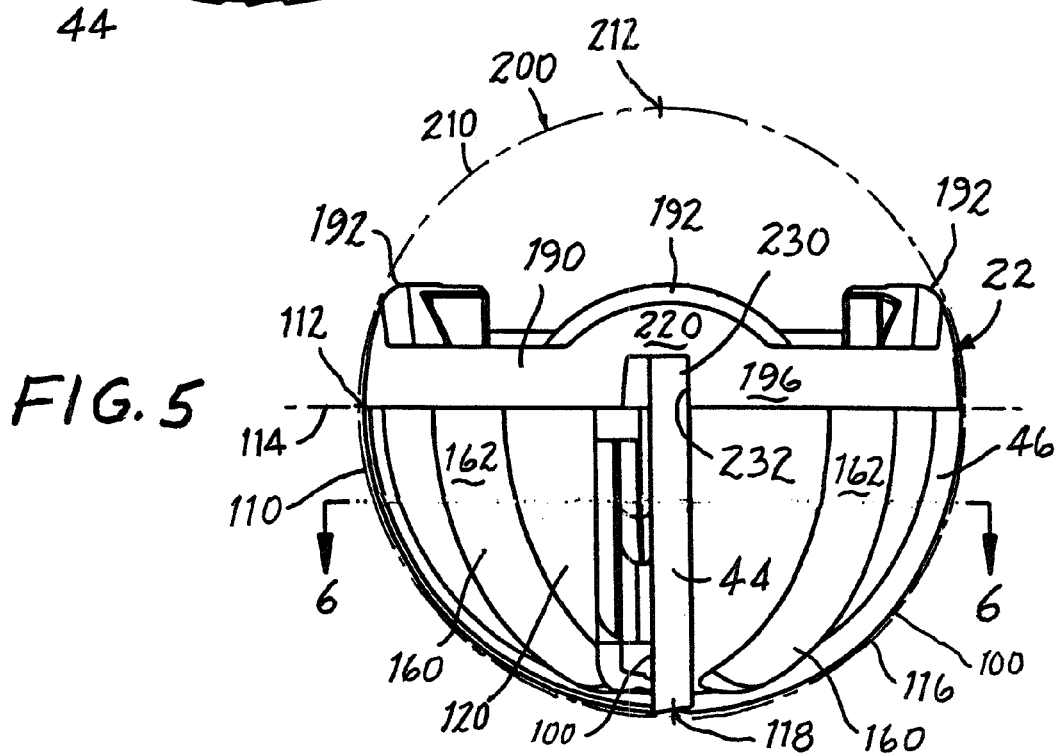
FIG. 5 is a side elevational view of the cutting head.

Turning now to FIGS. 2 and 3, as well as to FIG. 1, cutting head 22 extends in an axial direction from a distal end 32 to a proximal end 34 and is comprised of a cutting blade construct 40 and an arbor 42. The cutting blade construct 40 includes cutting elements in the form of cutting blades 44 and 46, each cutting blade 44 and 46 being constructed of a flat plate 48 of metal readily and economically cut from flat stock, such as sheet steel, as by stamping, blanking, punching or otherwise cutting a cutting blade 44 or 46 from a sheet of metal. Cutting blade 44 includes a first slot 50 which extends longitudinally along a central axis 52 of cutting blade 44, slot 50 being open at the proximal end 54 of cutting blade 44 and terminating adjacent to and spaced from the distal end 56 of cutting blade 44. Similarly, cutting blade 46 includes a second slot 60 which extends longitudinally along a central axis 62 of cutting blade 46, slot 60 being open at the distal end 64 of cutting blade 46 and terminating adjacent to and spaced from the proximal end 66 of cutting blade 46. The relative dimensions and location of the slots 50 and 60 enable the cutting blades 44 and 46 to be assembled readily into cutting blade construct 40 merely by placing the cutting blades 44 and 46 perpendicular to one another, aligning the slots 50 and 60 such that axes 52 and 62 are aligned coextensive with one another, and then interengaging the cutting blades 44 and 46 along the slots 50 and 60. Cutting blade construct 40 then includes four wings 70 extending in radial directions from a common central axis of rotation 72, the wings 70 being spaced apart circumferentially by 90°, as illustrated in FIG. 2 wherein cutting blade construct 40 is seen to have a generally cruciform configuration.

Referring now to FIGS. 4 through 10, as well as to FIGS. 1 through 3, arbor 42 includes grooves 74 and 76 oriented, dimensioned and configured for receiving cutting blades 44 and 46 upon insertion of cutting blade construct 40 into arbor 42, as indicated by the arrow 78 in FIG. 2. Thus, grooves 74 and 76 provide four branches 80 extending in radial directions from a common central axis of rotation 82 for receiving the four wings 70 of cutting blade construct 40, the orientation and relative dimensions of cutting blades 44 and 46 along wings 70 and branches 80 of grooves 74 and 76 establishing a fit between the cutting blade construct 40 and the arbor 42 wherein the wings 70 are supported and maintained in the generally cruciform configuration described above.

Once the cutting blade construct 40 is fully engaged within the arbor 42, the arbor 42 is coupled with the cutting blade construct 40 by a securing arrangement which includes detent elements in the form of protrusions 90 that project into branches 80 for entering counterpart apertures 92 in wings 70 to secure the wings 70 in place within branches 80 and thereby secure cutting blade construct 40 within arbor 42. In the preferred embodiment, arbor 42 is constructed of a synthetic polymeric material, such as a polycarbonate, and is molded in one piece. Protrusions 90 are molded unitary with arbor 42 and are deflected resiliently to enable insertion of cutting blade construct 40 into arbor 42, and then are snapped into apertures 92 to secure cutting blade construct 40 in place within arbor 42. Cutting head 22 then is ready to be coupled to operating handle 24 for executing a cutting operation. To that end, each cutting blade 44 and 46 is provided with a pair of arms 94 extending radially outwardly from a respective central axis 52, 62. Arms 94 establish an X-shaped coupling member 96 which is configured for ready selective coupling with coupling member 98 of coupling arrangement 26 to couple the cutting head 22 to the operating handle 24.

Surgical cutting tool 20 is constructed for cutting natural bone at an implant site for a prosthetic joint, the illustrated embodiment being dimensioned and configured for cutting a seating surface in an acetabulum in preparation for the reception of an acetabular component of a prosthetic hip joint. To that end, the wings 70 of the cutting blades 44 and 46 are provided with cutting edges 100 having a curved profile configuration such that upon rotation of the cutting blade construct 40 about central axis of rotation 72, the cutting edges 100 will follow a cutting envelope 110 having a curved contour configuration complementary to the curved contour configuration of the seating surface to be cut. In this instance, the curved contour configuration of the seating surface is a concave hemispherical contour configuration so that the contour configuration of the cutting envelope 110 is a convex hemispherical contour configuration for cutting a concave seating surface which will accommodate the domed configuration of the acetabular component to be implanted at the implant site being prepared. The hemispherical contour configuration of the cutting envelope 110 has an equator 112 lying in a generally radial proximal plane 114, and the cutting edges 100 extend along meridians 116, between a distal pole 118 and the equator 112.

Figure 6:
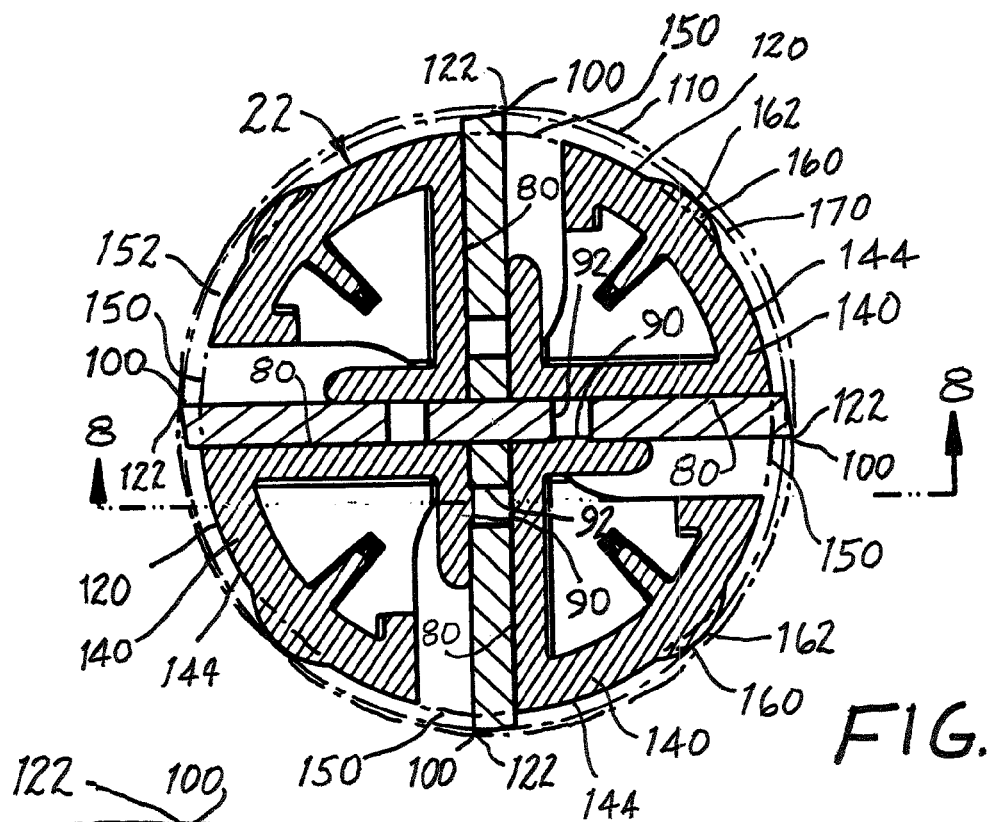
FIG. 6 is a cross-sectional view taken along line 6-6 of FIG. 5.
Figure 7:
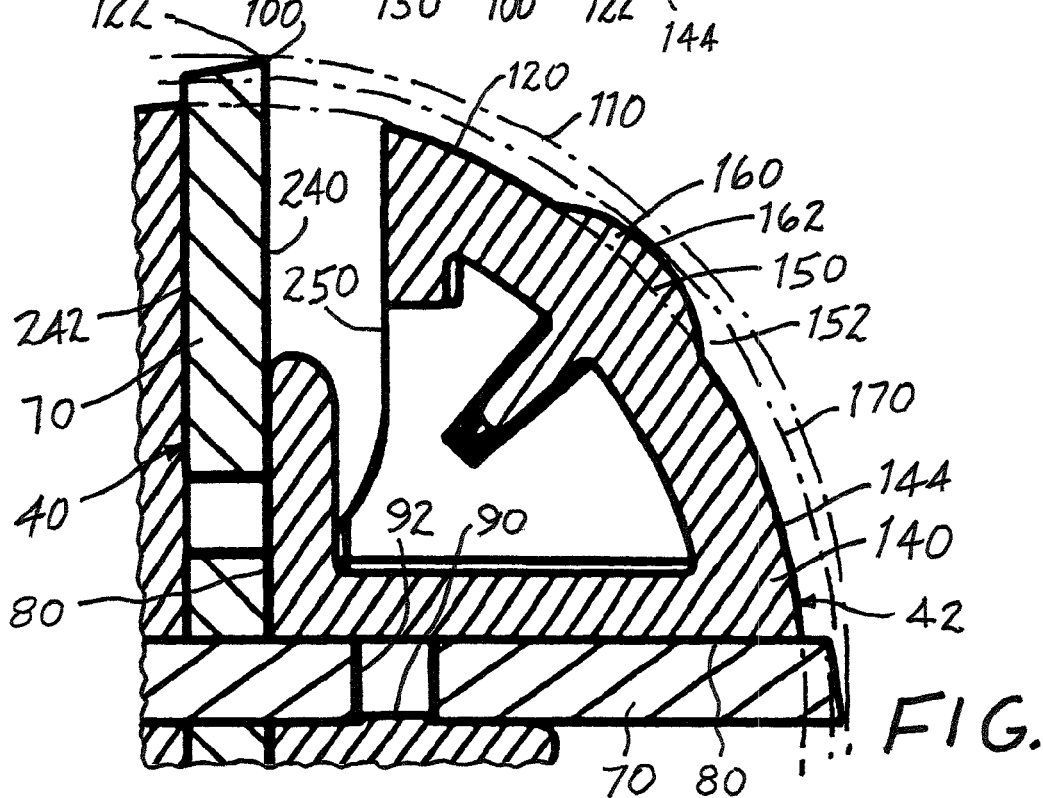
FIG. 7 is an enlarged fragmentary view showing a portion of FIG. 6.
Figure 8:
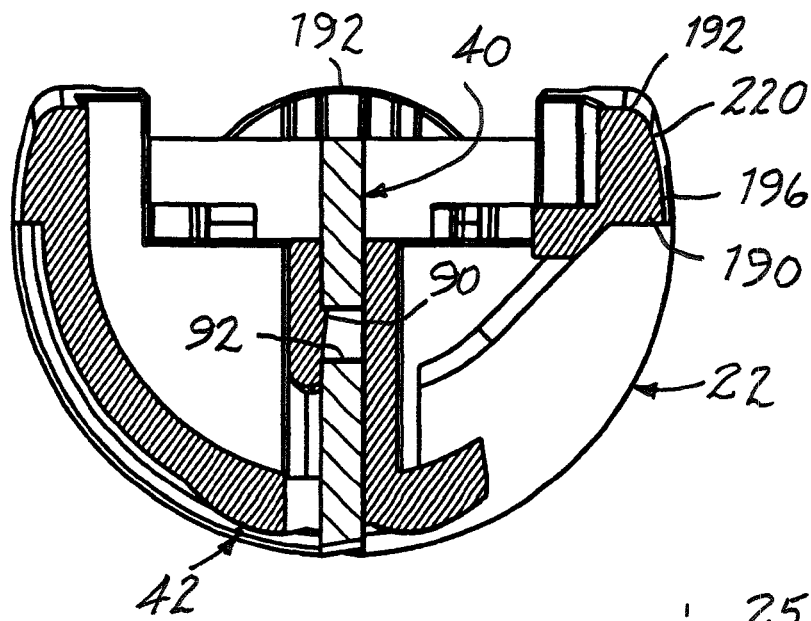
FIG. 8 is a cross-sectional view taken along line 8-8 of FIG. 6.
Figure 9:
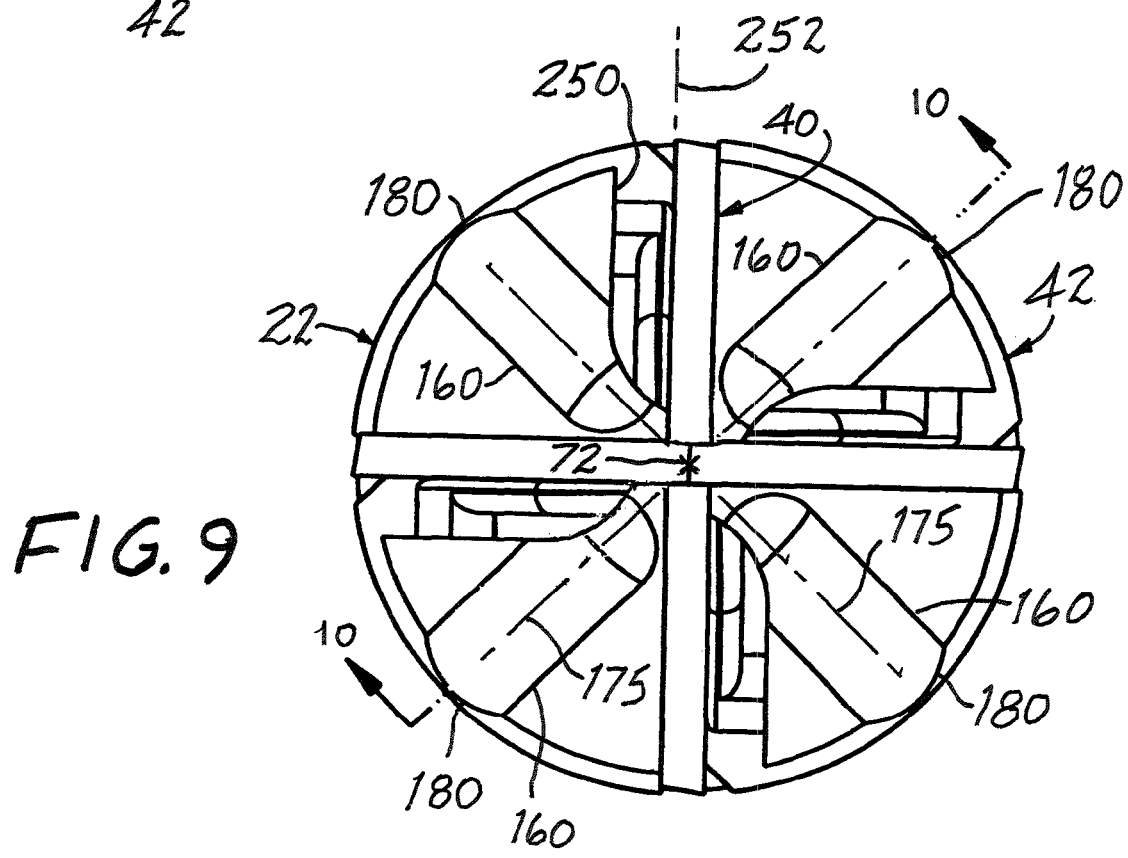
FIG. 9 is a bottom plan view the cutting head.
Figure 10:
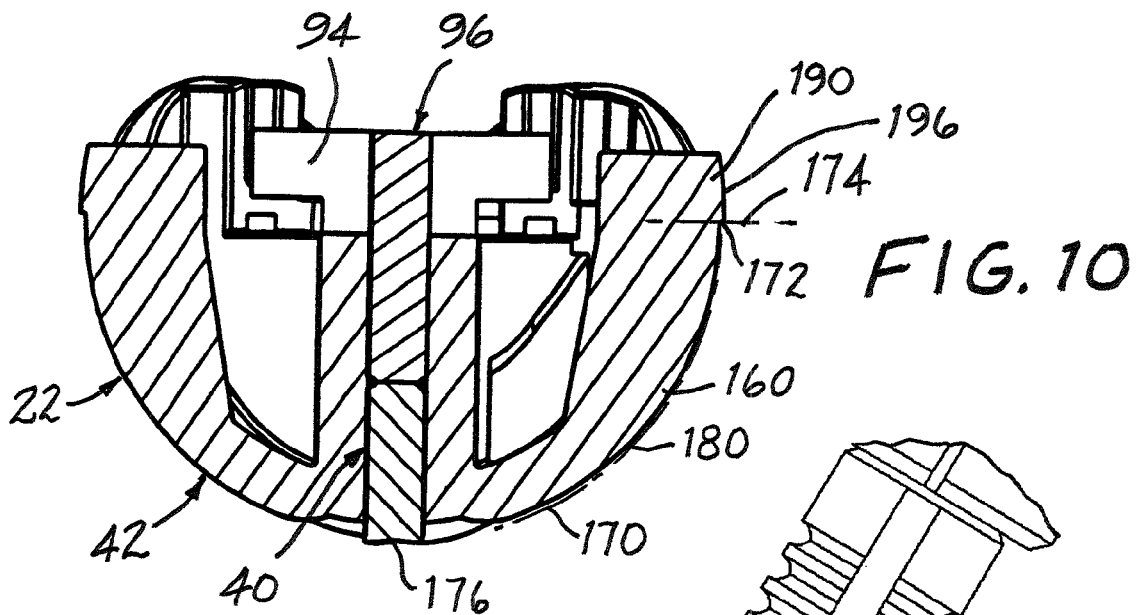
FIG. 10 is a cross-sectional view taken along line 10-10 of FIG. 9.

As best seen in FIGS. 6 and 7, as well as in FIGS. 1 through 5, and FIGS. 8 through 10, arbor 42 has an external surface 120 which, in the preferred construction, follows a generally convex curved hemispherical contour configuration, portions of which serve different functions, as will be described below. Once the cutting blade construct 40 is fully engaged with and secured within arbor 42, the cutting edges 100 are spaced radially away from the external surface 120 of the arbor 42, in this instance in an outward direction, to expose the cutting edges 100, as seen at 122, for cutting the curved contour configuration of the seating surface, illustrated at 130 in a diagrammatic depiction of an implant site 132. Arbor 42 includes segments 140 extending circumferentially between the wings 70 of the cutting blade construct 40 for supporting the wings 70 and, consequently, the cutting edges 100 spaced from one another circumferentially during a cutting operation.

External surface 120 of arbor 42 includes first surface portions 144 extending along a support envelope 150 spaced radially away from the cutting envelope 110, in this instance in an inward direction, as seen at 152. The inward spacing 152 of the support envelope 150 provides clearance between the external surface 120 and the natural bone, along first portions 144, during cutting of the seating surface 130, thereby reducing friction between the arbor 42 and the natural bone during preparation of implant site 132, while still providing support for the wings 70 of cutting blades 44 and 46 as the cutting edges 100 cut the natural bone.

In order to accomplish stability and better control of the cutting head 22 during the cutting operation, arbor 42 is provided with stabilizers shown in the form of ribs 160 which extend along external surface 120 of arbor 42 and include second surface portions 162 of the external surface 120 of arbor 42, the second surface portions 162 being located circumferentially intermediate circumferentially adjacent cutting edges 100 and spaced radially intermediate the support envelope 150 and the cutting envelope 110, the second surface portions 162 following a stabilizing envelope 170 for juxtaposition with the natural bone during cutting of the seating surface 130 so as to stabilize the cutting blade construct 40 while rotating the cutting head 22 about the central axis of rotation 72 to cut the seating surface 130. Stabilizing envelope 170 has a hemispherical contour configuration, which includes an equator 172 placed in a radial proximal plane 174, and is located radially intermediate the cutting envelope 110 and the support envelope 150. Ribs 160 are unitary with arbor 42, are located circumferentially intermediate circumferentially adjacent cutting edges 100, follow meridians of the stabilizing envelope 170, in axial planes 175, between a distal pole 176 and the equator 172, and have a convex curved profile configuration 180, as viewed in radial planes, which enables the second surface portions 162 to engage the seating surface 130, as the seating surface 130 is being cut, for providing stability to the cutting head 22 during the cutting operation, while facilitating rotation about the central axis of rotation 72. The stability provided by ribs 160 inhibits deleterious vibration and chattering of the cutting head 22 during the cutting operation, thereby promoting the creation of a smooth and accurate seating surface 130 having surface characteristics conducive to proper seating and affixation of an acetabular component.

Figure 11:
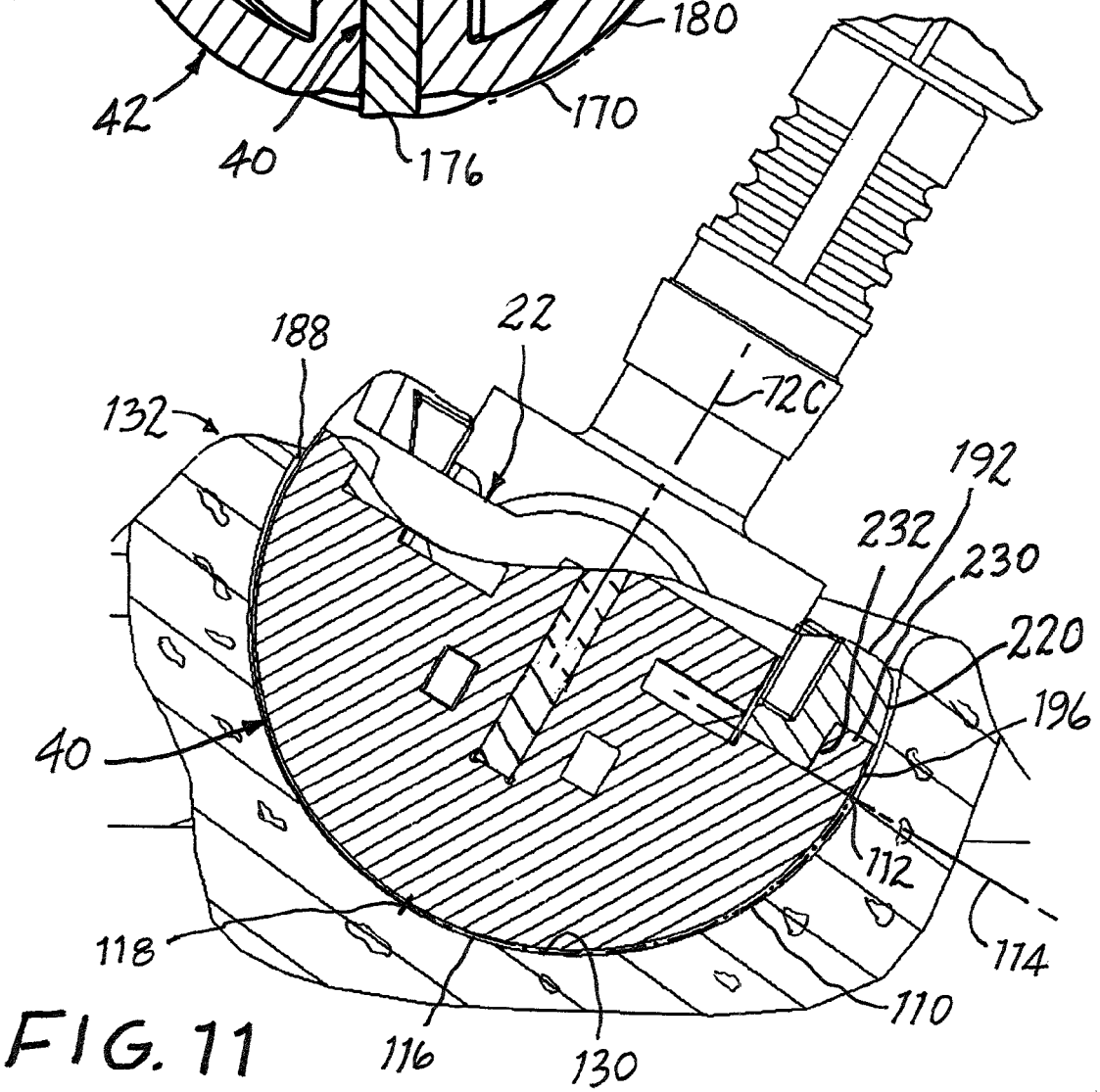
FIG. 11 is a somewhat diagrammatic side elevational view showing the surgical cutting tool in use.
Figure 14:
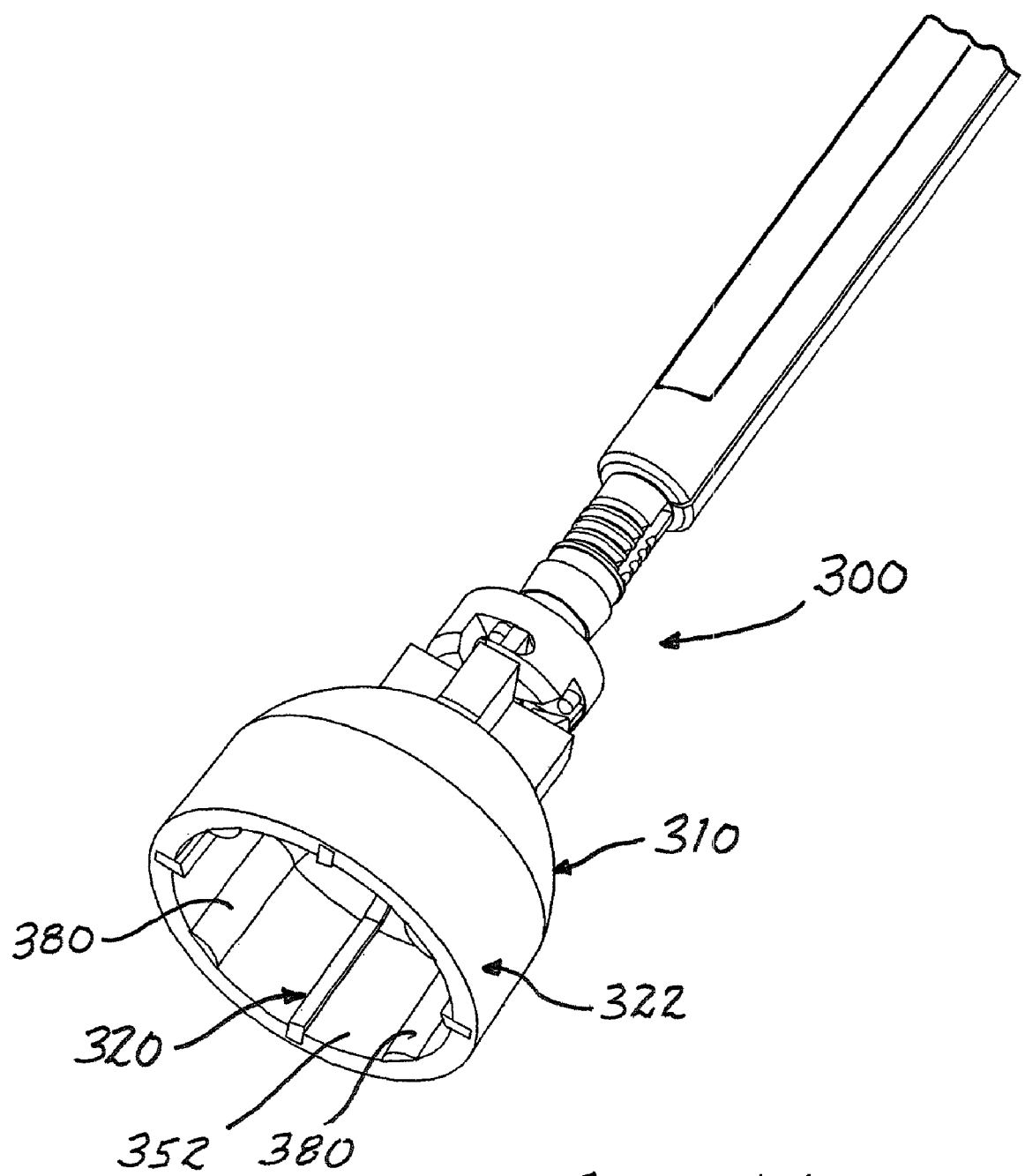
FIG. 14 is pictorial view, partially exploded, showing another surgical cutting tool constructed in accordance with the present invention.
Figure 15:
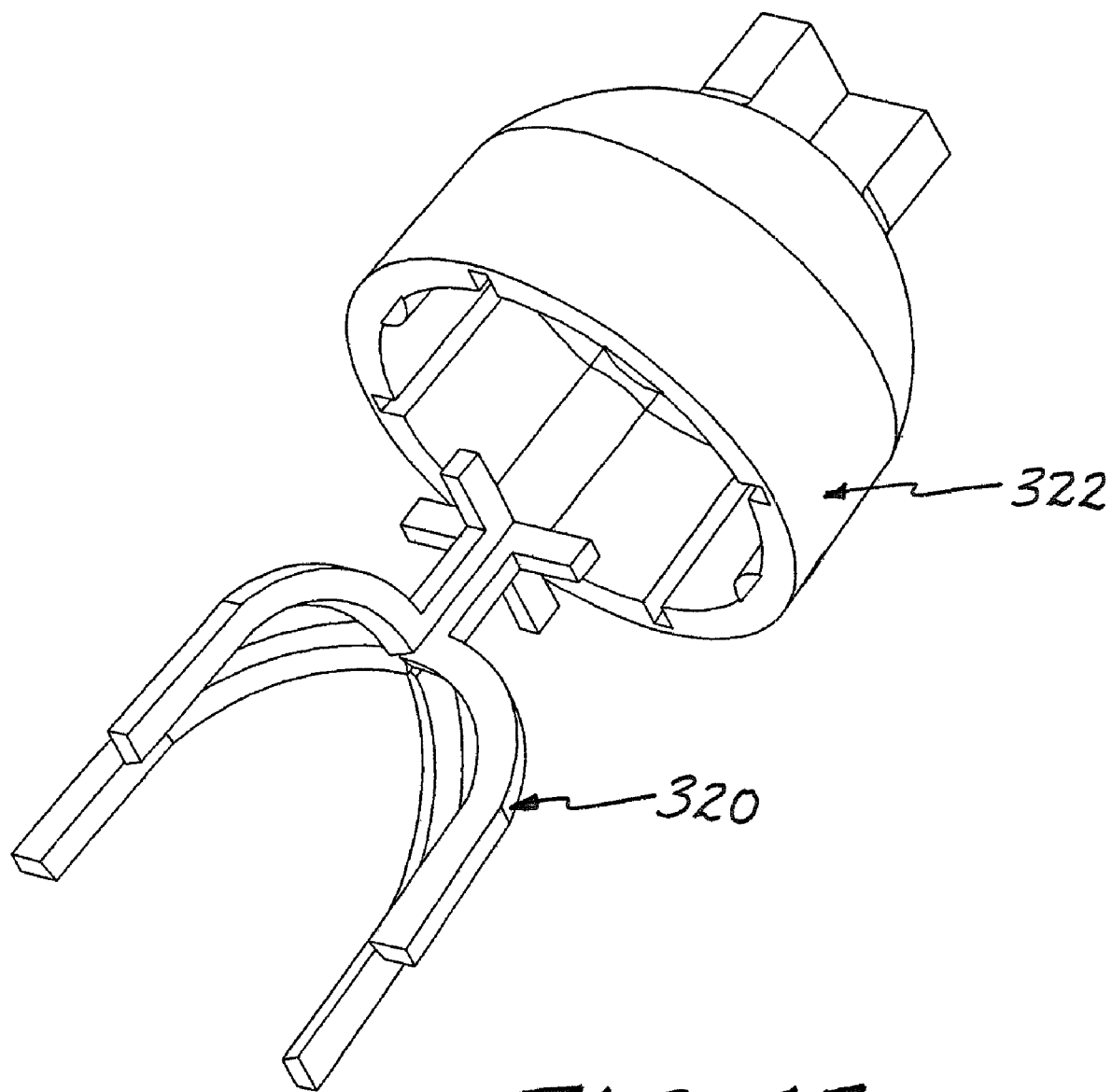
FIG. 15 is an exploded perspective view showing component parts of the surgical cutting tool of FIG. 14.
Figure 16:
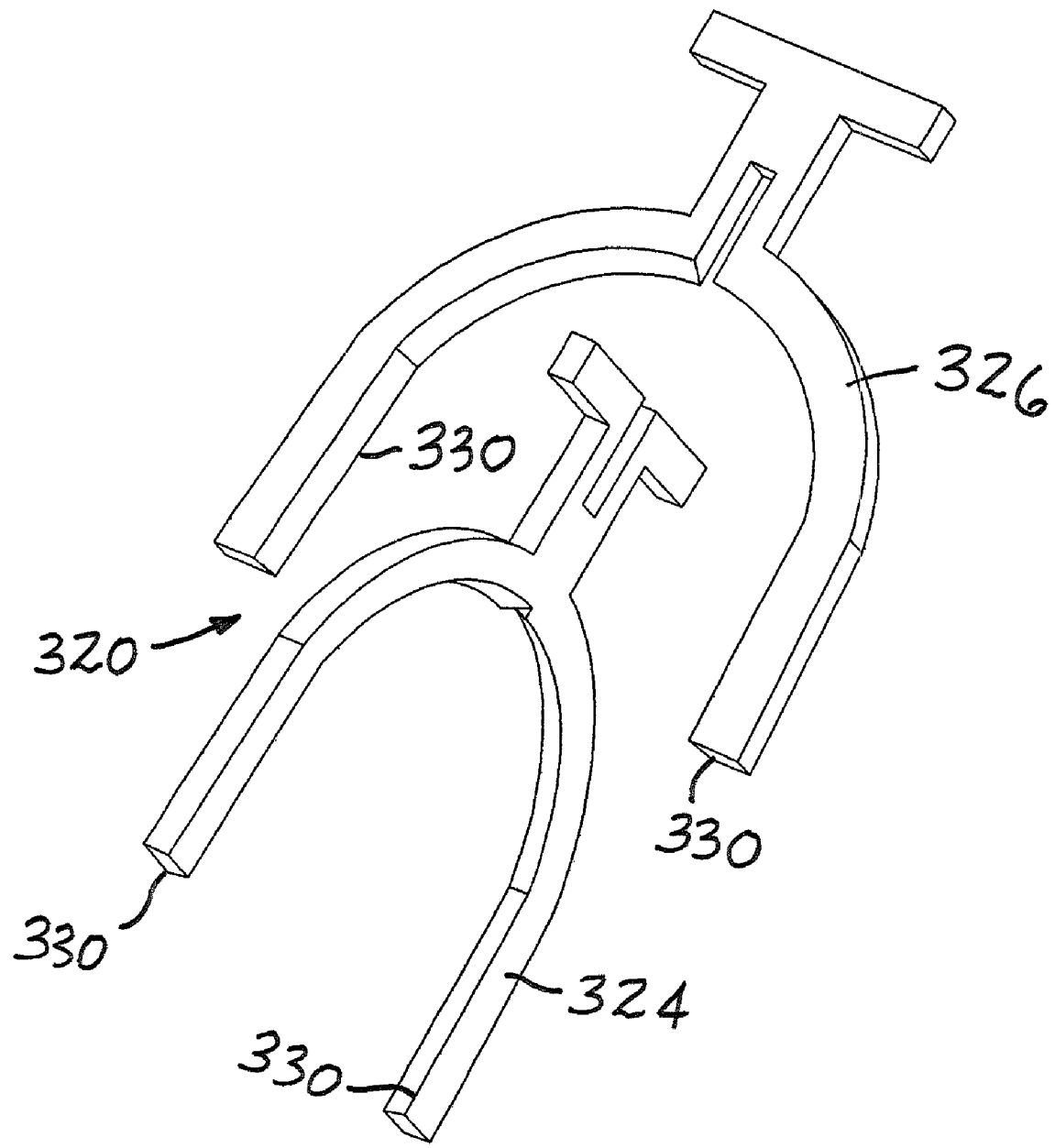
FIG. 16 is a further exploded perspective view showing component parts of the tool.
Figure 17:
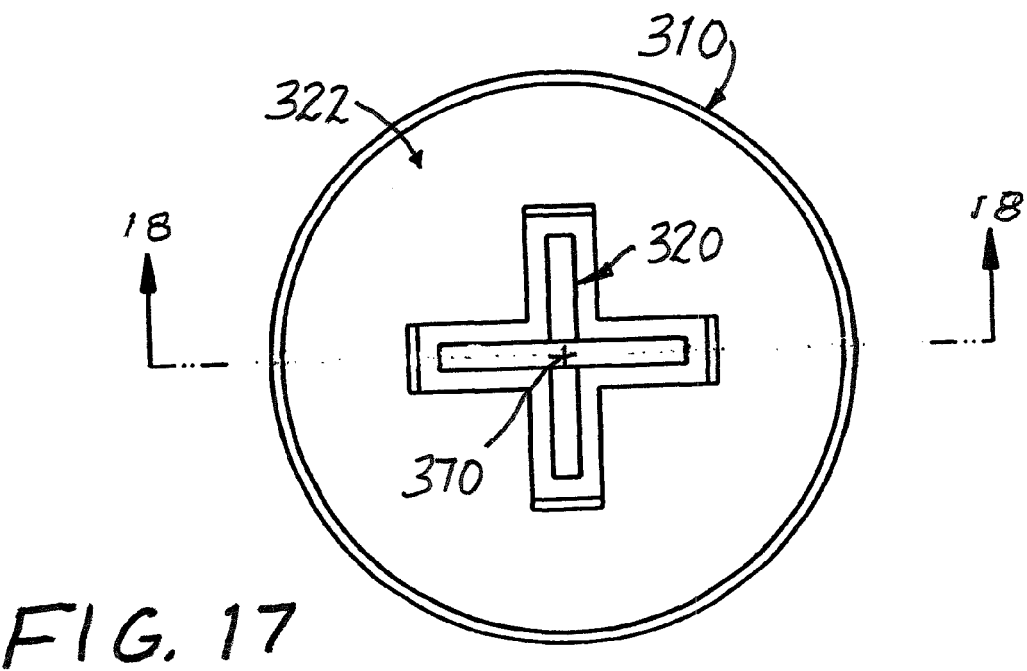
FIG. 17 is a top plan view of the cutting head of the surgical cutting tool of FIG. 14.
Figure 18:
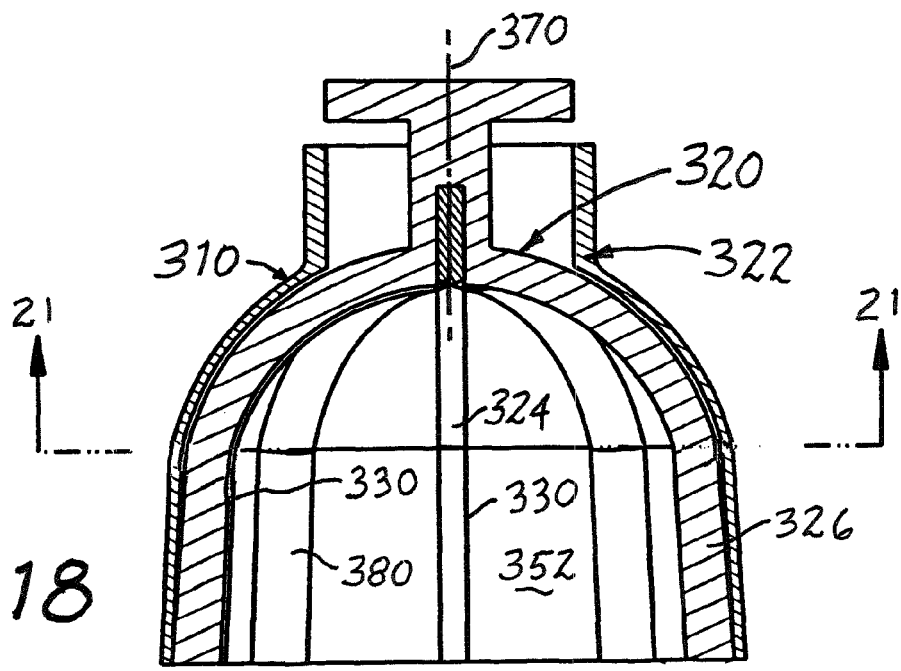
FIG. 18 is a longitudinal cross-sectional view taken along line 18-18 of FIG. 17.
Figure 19:
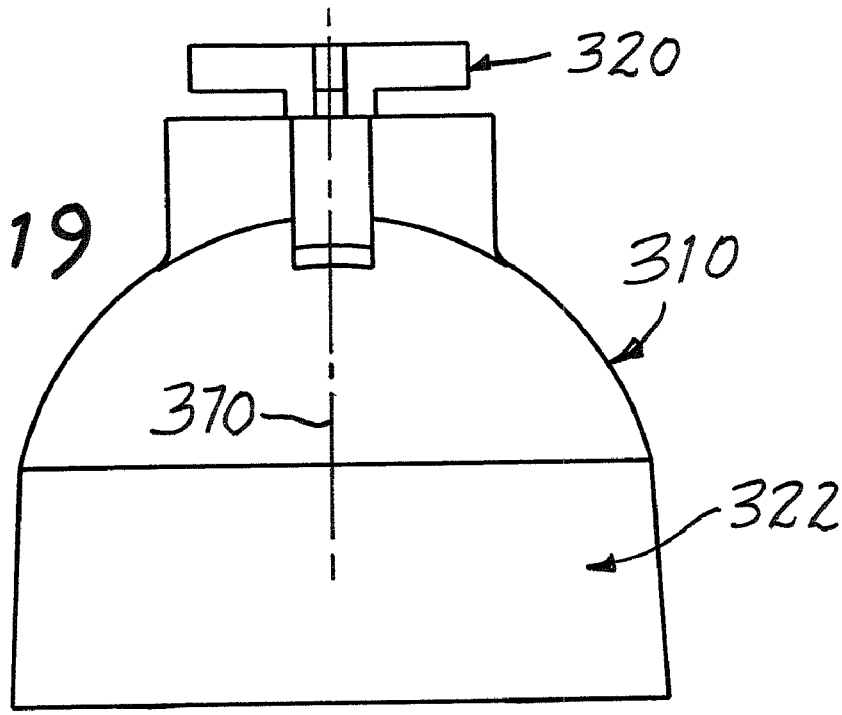
FIG. 19 is a side elevational view of the cutting head.
Figure 20:
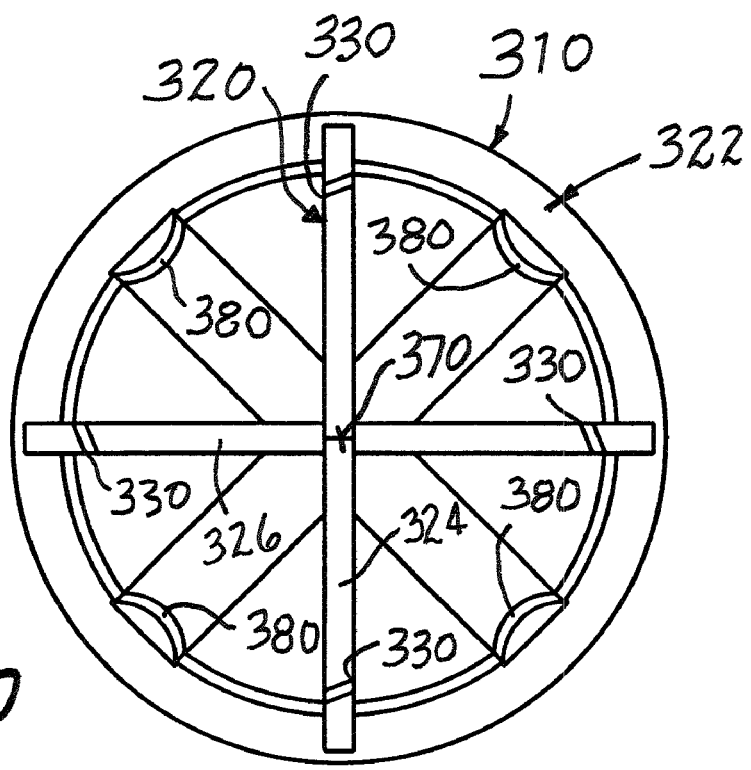
FIG. 20 is a bottom plan view of the cutting head.
Figure 21:
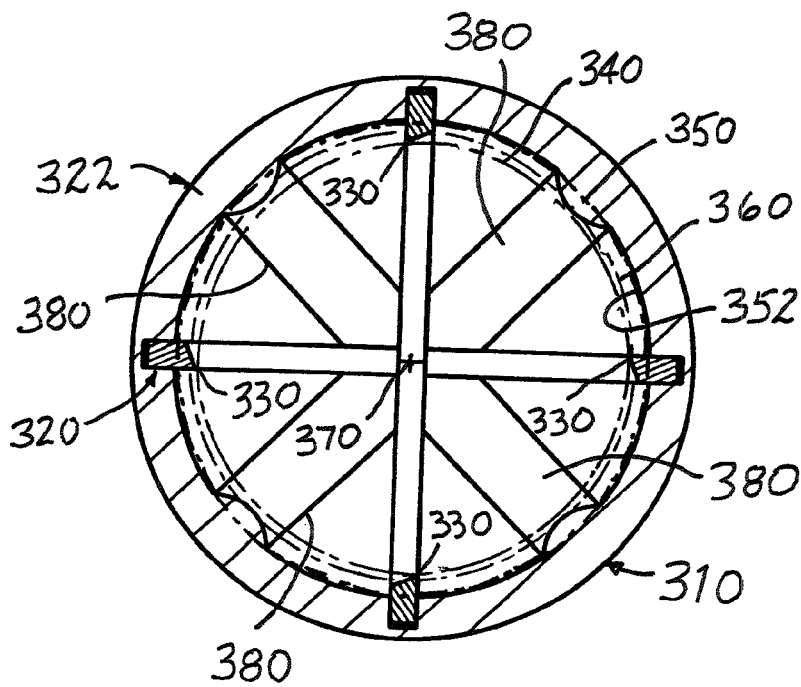
FIG. 21 is a cross-sectional view taken along line 21-21 of FIG. 18.
Figure 22:
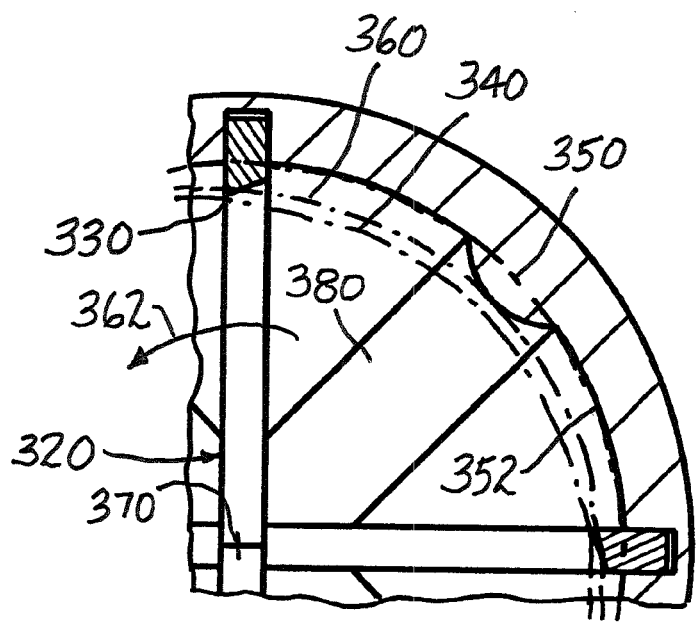
FIG. 22 is an enlarged fragmentary view showing a portion of FIG. 21.

The attainment of a smooth and accurate hemispherical surface throughout the entire seating surface 130, and particularly along the perimeter of the entrance to the seating surface 130, as depicted at 188 in FIG. 11, is facilitated by providing arbor 42 with a circular rim 190 located adjacent the equator 112 of the cutting envelope 110, and further stabilizers shown in the form of augments 192 contiguous with rim 190, spaced apart circumferentially along the rim 190, and extending in directions axially away from the distal pole 118 of the cutting envelope 110. Rim 190 has an outer surface 196 extending along a global envelope 200 which includes the cutting envelope 110 as a distal hemisphere of the global envelope 200, located between the distal pole 118 and the equator 112, and a proximal hemisphere 210 extending between the equator 112 and a proximal pole 212.

The augments 192 each provide an outer surface 220 having a semi-spherical surface contour configuration located on the proximal hemisphere 210 such that upon rocking of the central axis of rotation 72 during the cutting operation, as indicated in FIG. 11 by the canted disposition of central axis of rotation 72C, the outer surface 196 of the rim 190 and outer surfaces 220 of the augments 192 will engage the seating surface 130 as that seating surface 130 is being cut, and will guide and stabilize the cutting head 22 while accomplishing an accurate contour configuration in the seating surface 130 along the entrance 188 to the seating surface 130. The stability gained from enabling surfaces 220 to be located coincident with cutting envelope 110 serves to preclude cutting at these surfaces 220 and prevents unwanted migration of the cutting head 22 during the cutting operation. In addition, a tab 230 of each wing 70 of the cutting blades 44 and 46 is fitted into a corresponding slot 232 in the rim 190, at each augment 192, to assist in maintaining a precise location of the cutting blades 44 and 46, and the cutting blade construct 40, within the arbor 42.

Each wing 70 of the cutting blades 44 and 46 includes a leading face 240 and a trailing face 242. Arbor 42 is provided with a channel 250 juxtaposed with each leading face 240 and extending contiguous with the corresponding wing 70, following meridians of the support envelope 150, in axial planes 252, in the direction from the distal end 32 toward the proximal end 34 of the cutting head 22, for carrying away bone cut from the natural bone by the corresponding cutting edge 100 during cutting of the seating surface 130, the cut bone being carried along channels 250 in directions from the distal pole 118 toward the equator 112 of the cutting envelope 110.

Turning now to FIGS. 12 and 13, as well as to FIGS. 1 through 11, each cutting blade 44 and 46 is manufactured economically by merely stamping, blanking, punching or otherwise cutting a blade from flat stock, such as a flat plate of metal, and then creating cutting edges 100, as by grinding or utilizing a relatively simple edge-forming technique, without requiring bending or another forming operation to complete the manufacture of a cutting blade 44 or 46. Thus, each cutting blade 44 and 46 remains essentially flat, with generally planar leading and trailing faces 240 and 242, and an essentially uniform, predetermined thickness T throughout, thereby conserving manufacturing cost. The cutting blades 44 and 46 then are assembled readily to establish cutting blade construct 40.

As seen diagrammatically in FIGS. 12 and 13, each cutting blade 44 and 46 has a diameter D which extends along a centerline 260 placed intermediate leading face 240 and trailing face 242 of each wing 70, the diameter D being centered between the leading face 240 and the trailing face 242 of each wing 70. Consequently, within the cutting blade construct 40, each wing 70 has a radius R extending radially from the central axis of rotation 72 to the radially outer perimeter of the wing 70. The cutting edge 100 of each wing 70 is located at the corresponding leading face 240, spaced circumferentially forward of the centerline 260, in the direction of rotation of the cutting blade construct 40 during a cutting operation, the direction of rotation being indicated by arrow 266, and the trailing face 242 is spaced circumferentially back from the centerline 260, the spacing of each face 240 and 242 from centerline 260 being in accordance with the thickness T of the cutting blade 44 or 46. Since the cutting blades 44 and 46 each have a finite predetermined thickness T, and since the cutting blades 44 and 46 remain essentially flat, for economy of manufacture, cutting edges 100 intercept the cutting envelope 110 circumferentially forward of the centerline 260 and, consequently, forward of radius R. Radius R is different from, and in this instance smaller than, the corresponding radius RR of the cutting envelope 110, with the result that radius R is spaced radially inwardly from radius RR, thereby establishing a small gap 280 between the radius R and the cutting envelope 110, the gap 280 being located behind each cutting edge 100. The gap 280 established by the relative dimensions of radius R and radius RR, together with the circumferentially forward location of cutting edge 100, provides cutting blades 44 and 46 with an effective cutting profile 282 adjacent cutting edges 100 and facilitates exemplary cutting performance upon rotation of the cutting blade construct 40 in direction 266 to cut seating surface 130, with the cutting edge 100 along the cutting profile 282 engaging the cutting envelope 110 circumferentially forward of the gap 280.

It will be seen, then, that the construction which enables cutting blades 44 and 46 to be manufactured readily from simple flat stock provides enhanced cutting performance as well as economy. Further economy is realized by molding arbor 42 in a unitary structure of synthetic polymeric material, such as a polycarbonate. The assembled cutting blade construct 40 and arbor 42 is manufactured with such economy as to render the cutting head 22 expendable and enable the use of a fresh cutting head 22 with an unused, sharp cutting blade construct 40 in each procedure for the preparation of a suitable seating surface at an implant site.

Referring now to FIGS. 14 through 24, another surgical cutting tool constructed in accordance with the present invention is shown at 300 and is seen to include an alternate cutting head 310, constructed for cutting a seating surface having a convex curved contour configuration, such as, for example, the domed surface of a femoral head. In a construction similar to that described above in connection with surgical cutting tool 20, cutting head 310 is comprised of a cutting blade construct 320 assembled with an arbor 322. In this instance, however, cutting blades 324 and 326 of the cutting blade construct 320 include cutting edges 330, each of which extends along a concave curved profile configuration for following a concave hemispherical cutting envelope 340. A support envelope 350 is spaced radially outwardly from the cutting envelope 340, and a support surface 352 extends along the support envelope 350. A stabilizing envelope 360 is located radially intermediate the cutting envelope 340 and the support envelope 350.

Rotation of cutting head 310 in the direction 362 about central axis of rotation 370 will enable the cutting edges 330 to cut a convex hemispherical seating surface corresponding to the contour configuration of the cutting envelope 340. Stabilizers in the form of ribs 380 are arrayed circumferentially around the surface 352 of the arbor 322, circumferentially intermediate the cutting edges 330, and extend along the stabilizing envelope 360 to provide stability and accuracy during the cutting operation. [Channels 388 are juxtaposed with the leading faces 390 of the cutting blades 324 and 326 for carrying away cut bone.]

As before, and as now best seen in FIGS. 23 and 24, cutting blades 324 and 326 are constructed of essentially flat stock, the flat stock having a predetermined thickness T which places the cutting edges 330 circumferentially forward of the radius RI of each wing 390 of the cutting blade construct 320 so that the radius RI is different from, and in this instance somewhat larger than, the radius RC of the cutting envelope 340. Radius RI then is spaced from the cutting envelope 340 by a gap 392 established by the relative dimensions of radius RI and radius RC and is placed circumferentially behind each cutting edge 330 to attain the desired effective cutting profile 394 adjacent cutting edges 330. Manufacturing economy is realized through maintaining the essentially flat configuration of the cutting blades 324 and 326, while cutting performance is enhanced by virtue of the gaps 392 placed behind the cutting edges 330 and cutting profile 394.

It will be seen that the present invention attains the several objects and advantages summarized above, namely: Enables a higher degree of accuracy, with increased ease, in the preparation of natural bone at an implant site for the reception of an implant component of a prosthetic joint; provides a less costly surgical cutting tool, readily manufactured to closer tolerances, for more effectively cutting an accurate seating surface, with increased ease, for an implant component of a prosthetic joint, and especially for the preparation of an acetabulum to receive an acetabular component; enables the establishment of a seating surface for the reception of an implant component, and especially an acetabular surface for the reception of an acetabular component, the seating surface being relatively smooth and uninterrupted by unwanted peaks and valleys so as to be more conducive to proper placement and affixation of the implant component; provides a construction in a surgical cutting tool for use in the preparation of an implant site, the tool being manufactured with such economy as to render the tool readily expendable, thereby enabling economical use of a new, freshly sharp cutting tool with each implant procedure.

It is to be understood that the above detailed description of preferred embodiments of the invention are provided by way of example only. Various details of design and construction may be modified without departing from the true spirit and scope of the invention, as set forth in the appended claims.

The embodiments of the invention in which an exclusive property or privilege is claimed are defined as follows:

1. A surgical cutting tool for cutting a seating surface in natural bone, the seating surface having a contour configuration for receiving a component of a prosthetic implant having a complementary contour configuration, the cutting tool comprising:

a cutting blade construct including a central axis of rotation and at least one cutting element having at least one cutting edge spaced from the central axis in a radial direction, the cutting edge having a profile configuration dimensioned and configured such that upon rotation of the cutting blade construct about the central axis of rotation, the cutting edge will follow a cutting envelope having a contour configuration for corresponding to the contour configuration of the seating surface; and an arbor coupled with the cutting blade construct for rotation about the central axis of rotation with the cutting blade construct, the arbor having an external surface;

the cutting blade construct being placed within the arbor with the cutting edge juxtaposed in close proximity with and spaced radially away from the external surface of the arbor to expose the cutting edge for cutting the contour configuration of the seating surface, and the arbor extending circumferentially adjacent to and in close proximity with the exposed cutting edge for supporting the cutting edge in circumferential directions;

the external surface of the arbor including first surface portions extending along a support envelope juxtaposed in close proximity with and spaced at a predetermined fixed distance radially away from the cutting envelope such that upon rotation of the arbor during cutting of the seating surface the support envelope will be juxtaposed in close proximity with and spaced radially from the natural bone, and second surface portions located circumferentially adjacent the cutting edge, and at a fixed location radially intermediate and juxtaposed in close proximity with the support envelope and the cutting envelope to follow a stabilizing envelope for juxtaposition and engagement with the natural bone during cutting of the seating surface to stabilize the cutting blade construct within the natural bone while rotating the arbor and cutting blade construct about the central axis of rotation to cut the seating surface.

2. The surgical cutting tool of claim 1 wherein the cutting blade construct includes cutting elements having cutting edges spaced from one another in circumferential directions, and spaced from the central axis in radial directions, the cutting blade construct being placed within the arbor with the cutting edges spaced radially away from the external surface of the arbor to expose the cutting edges for cutting the contour configuration of the seating surface, and the arbor extending circumferentially between the cutting elements for supporting the cutting edges spaced from one another in circumferential directions, and the second surface portions are located circumferentially intermediate circumferentially adjacent cutting edges.

3. The surgical cutting tool of claim 2 wherein the seating surface has a curved contour configuration for receiving a component of a prosthetic implant having a complementary curved contour configuration, each cutting edge has a curved profile configuration, the cutting envelope has a curved contour configuration for corresponding to the curved contour configuration of the seating surface, and the cutting envelope comprises a hemispherical contour configuration having an equator lying in a generally radial proximal plane and the cutting edges extend along meridians lying in axial planes and extending between a distal pole and the equator.

4. The surgical cutting tool of claim 3 wherein the curved contour configuration of the seating surface is concave and the curved contour configuration of the cutting envelope is convex.

5. The surgical cutting tool of claim 3 wherein the curved contour configuration of the seating surface is convex and the curved contour configuration of the cutting envelope is concave.

6. The surgical cutting tool of claim 3 wherein the stabilizing envelope comprises a hemispherical contour configuration having an equator lying in a generally radial proximal plane and the arbor includes at least one stabilizer extending along a meridian lying in an axial plane and extending between a distal pole and the equator, the stabilizer being located circumferentially adjacent a respective cutting edge and radially intermediate the support envelope and the cutting envelope, one of the second surface portions being located along the stabilizers.

7. The surgical cutting tool of claim 3 wherein the stabilizing envelope comprises a hemispherical contour configuration having an equator lying in a generally radial proximal plane and the arbor includes stabilizers extending along respective meridians lying in axial planes extending between the distal pole and the equator, the stabilizers being located circumferentially intermediate circumferentially adjacent cutting edges and radially intermediate the support envelope and the cutting envelope, the second surface portions being located along the stabilizers.

8. The surgical cutting tool of claim 7 wherein the stabilizers each comprise a rib integral with the arbor and having a convex curved profile configuration in radial planes.

9. The surgical cutting tool of claim 7 wherein the cutting envelope comprises a hemispherical contour configuration having an equator lying in a generally radial proximal plane, and the arbor includes a generally circular rim extending around the equator of the cutting envelope, and at least one further stabilizer on the rim, the further stabilizer having a surface contour configuration for engaging the natural bone to further stabilize the arbor upon rocking of the central axis of rotation during cutting of the seating surface.

10. The surgical cutting tool of claim 7 wherein the cutting envelope comprises a hemispherical contour configuration having an equator lying in a generally radial proximal plane, and the arbor includes a generally circular rim extending around the equator of the cutting envelope, and further stabilizers spaced circumferentially around the rim, each further stabilizer having a surface contour configuration for engaging the natural bone to further stabilize the arbor upon rocking of the central axis of rotation during cutting of the seating surface.

11. The surgical cutting tool of claim 10 wherein the further stabilizers each comprise an augment extending in an axial direction away from the distal pole, and the surface contour configuration of each further stabilizer comprises a part-spherical surface contour configuration.

12. The surgical cutting tool of claim 11 wherein the part-spherical surface contour configuration is dimensioned and configured to correspond to the contour configuration of the cutting envelope.

13. The surgical cutting tool of claim 8 wherein the curved contour configuration of the seating surface is concave and the curved contour configuration of the cutting envelope is convex.

14. The surgical cutting tool of claim 8 wherein the curved contour configuration of the seating surface is convex and the curved contour configuration of the cutting envelope is concave.

15. The surgical cutting tool of claim 2 wherein the cutting blade construct is constructed of metal, and the arbor is constructed of a synthetic polymeric material.

16. The surgical cutting tool of claim 2 wherein each cutting element includes a leading face for engaging the natural bone during cutting of the seating surface, and the arbor includes a channel juxtaposed with the leading face of each cutting element and extending along a respective cutting element for carrying away bone cut from the natural bone by a corresponding cutting edge during cutting of the seating surface.

17. The surgical cutting tool of claim 16 wherein the support envelope comprises a hemispherical contour configuration having an equator lying in a generally radial proximal plane and the channels extend along respective meridians lying in axial planes and extending between a distal pole and the equator for carrying cut bone toward the equator during cutting of the seating surface.

18. The surgical cutting tool of claim 2 wherein each cutting element comprises a cutting blade of predetermined thickness, each cutting blade extending along a radius of the cutting envelope to place a corresponding cutting edge on the cutting envelope and having a leading face and a trailing face spaced circumferentially back from the leading face by the predetermined thickness of the cutting blade, each cutting blade extending from the central axis of rotation radially along a cutting blade radius and being located such that the central axis of rotation is placed intermediate the leading face and the trailing face of each corresponding cutting blade and each corresponding cutting blade radius extends intermediate the leading face and the trailing face throughout each cutting blade, the relative dimensions of the cutting blade radius and a corresponding radius of the cutting envelope establishing a gap between the cutting blade radius and the cutting envelope and a cutting profile along the cutting blade, each gap being located circumferentially between a corresponding cutting edge and at least one of an adjacent leading face and an adjacent trailing face, such that upon rotation of the cutting blade construct to cut the seating surface, the cutting edge along the cutting profile will engage the natural bone along the cutting envelope circumferentially spaced from the one of the adjacent leading face and the adjacent trailing face.

19. The surgical cutting tool of claim 2 wherein each cutting element comprises a cutting blade of predetermined thickness, each cutting blade extending along a radius of the cutting envelope to place a corresponding cutting edge on the cutting envelope and having a leading face at the cutting edge for engaging the natural bone during cutting of the seating surface, and a trailing face spaced circumferentially back from the leading face by the predetermined thickness of the cutting blade, each cutting blade extending from the central axis of rotation radially along a cutting blade radius and being located such that the central axis of rotation is placed intermediate the leading face and the trailing face of each corresponding cutting blade and each corresponding cutting blade radius extends intermediate the leading face and the trailing face throughout each cutting blade, the relative dimensions of the cutting blade radius and a corresponding radius of the cutting envelope establishing a gap between the cutting blade radius and the cutting envelope and a cutting profile along the cutting blade, each gap being located circumferentially behind a corresponding cutting edge, and the leading face being spaced circumferentially forward of the cutting blade radius such that upon forward rotation of the cutting blade construct to cut the seating surface, the cutting edge along the cutting profile will engage the natural bone along the cutting envelope circumferentially forward of the gap.

20. The surgical cutting tool of claim 19 wherein the cutting blade radius is less than the corresponding radius of the cutting envelope.

21. The surgical cutting tool of claim 19 wherein the cutting blade radius is located essentially centrally between the leading face and the trailing face.

22. The surgical cutting tool of claim 19 wherein the cutting blade extends along a cutting blade diameter coincident with and different from a corresponding diameter of the cutting envelope, and the cutting blade radius extends along the cutting blade diameter.

23. The surgical cutting tool of claim 22 wherein the cutting blade diameter is less than the corresponding diameter of the cutting envelope.

24. The surgical cutting tool of claim 22 wherein the cutting elements comprise at least two cutting blades interengaged to establish a generally cruciform configuration in the cutting blade construct.

25. The surgical cutting tool of claim 24 wherein the cutting blade radius is located essentially centrally between the leading face and the trailing face.

26. A surgical cutting tool for cutting a seating surface in natural bone, the seating surface having a contour configuration for receiving a component of a prosthetic implant having a complementary contour configuration, the cutting tool comprising:

a cutting blade construct including a central axis of rotation and cutting elements having cutting edges spaced from one another in circumferential directions, and spaced from the central axis in radial directions, each cutting edge having a profile configuration dimensioned and configured such that upon rotation of the cutting blade construct about the central axis of rotation, the cutting edges will follow a cutting envelope having a contour configuration for corresponding to the contour configuration of the seating surface; and an arbor coupled with the cutting blade construct for rotation about the central axis of rotation with the cutting blade construct, the arbor having an external surface;

the cutting blade construct being placed within the arbor with the cutting edges spaced radially away from the external surface of the arbor to expose the cutting edges for cutting the profile contour configuration of the seating surface, and the arbor extending circumferentially between the cutting elements for supporting the cutting edges spaced from one another in circumferential directions;

each cutting element comprising a cutting blade of predetermined thickness, each cutting blade extending along a radius of the cutting envelope to place a corresponding cutting edge on the cutting envelope and having a leading face and a trailing face spaced circumferentially back from the leading face by the predetermined thickness of the cutting blade, each cutting blade extending from the central axis of rotation radially along a cutting blade radius and being located such that the central axis of rotation is placed intermediate the leading face and the trailing face of each corresponding cutting blade and each corresponding cutting blade radius extends intermediate the leading face and the trailing face throughout each cutting blade, the relative dimensions of the cutting blade radius and a corresponding radius of the cutting envelope establishing a gap between the cutting blade radius and the cutting envelope and a cutting profile along the cutting blade, each gap being located circumferentially between a corresponding cutting edge and at least one of an adjacent leading face and an adjacent trailing face, such that upon rotation of the cutting blade construct to cut the seating surface, the cutting edge along the cutting profile will engage the natural bone along the cutting envelope circumferentially spaced from the one of the adjacent leading face and the adjacent trailing face.

27. A surgical cutting tool for cutting a seating surface in natural bone, the seating surface having a contour configuration for receiving a component of a prosthetic implant having a complementary contour configuration, the cutting tool comprising:

a cutting blade construct including a central axis of rotation and cutting elements having cutting edges spaced from one another in circumferential directions, and spaced from the central axis in radial directions, each cutting edge having a profile configuration dimensioned and configured such that upon rotation of the cutting blade construct about the central axis of rotation, the cutting edges will follow a cutting envelope having a contour configuration for corresponding to the contour configuration of the seating surface; and an arbor coupled with the cutting blade construct for rotation about the central axis of rotation with the cutting blade construct, the arbor having an external surface;

the cutting blade construct being placed within the arbor with the cutting edges spaced radially away from the external surface of the arbor to expose the cutting edges for cutting the profile contour configuration of the seating surface, and the arbor extending circumferentially between the cutting elements for supporting the cutting edges spaced from one another in circumferential directions;

each cutting element comprising a cutting blade extending along a radius of the cutting envelope, each cutting blade having a predetermined thickness, a leading face at the cutting edge for engaging the natural bone during cutting of the seating surface, and a trailing face spaced circumferentially back from the leading face by the predetermined thickness of the cutting blade, each cutting blade extending from the central axis of rotation radially along a cutting blade radius and being located such that the central axis of rotation is placed intermediate the leading face and the trailing face of each corresponding cutting blade and each corresponding cutting blade radius extends intermediate the leading face and the trailing face throughout each cutting blade, the relative dimensions of the cutting blade radius and a corresponding radius of the cutting envelope establishing a gap between the cutting blade radius and the cutting envelope and a cutting profile along the cutting blade, each gap being located circumferentially behind a corresponding cutting edge, and the leading face being spaced circumferentially forward of the cutting blade radius such that upon rotation of the cutting blade construct to cut the seating surface, the cutting edge along the cutting profile will engage the natural bone along the cutting envelope circumferentially forward of the gap.

28. The surgical cutting tool of claim 27 wherein the cutting blade radius is less than the corresponding radius of the cutting envelope.

29. The surgical cutting tool of claim 27 wherein the cutting blade radius is located essentially centrally between the leading face and the trailing face.

30. The surgical cutting tool of claim 27 wherein the cutting blade extends along a cutting blade diameter coincident with and less than a diameter of the cutting envelope, and the cutting blade radius extends along the cutting blade diameter.

31. The surgical cutting tool of claim 30 wherein the cutting elements comprise at least two cutting blades interengaged to establish a generally cruciform configuration in the cutting blade construct.

32. The surgical cutting tool of claim 31 wherein the cutting blade radius is located essentially centrally between the leading face and the trailing face.

33. The surgical cutting tool of claim 1 wherein
  the cutting blade construct is constructed of metal, and the arbor is constructed of a synthetic polymeric material.

34. The surgical cutting tool of claim 33 wherein the arbor comprises a unitary structure.

\* \* \* \* \*